United States Patent

Sakakibara et al.

Patent Number: 5,840,699
Date of Patent: Nov. 24, 1998

[54] PEPTIDE DERIVATIVES

[75] Inventors: Kyoichi Sakakibara, Tokyo; Masaaki Gondo, Yokohama; Koichi Miyazaki, Ebina; Takeshi Ito, Kawasaki; Akihiro Sugimura, Kawasaki; Motohiro Kobayashi, Kawasaki, all of Japan

[73] Assignee: Teikoku Hormone Mfg. Co. Ltd., Tokyo, Japan

[21] Appl. No.: 945,211

[22] PCT Filed: Apr. 8, 1996

[86] PCT No.: PCT/JP96/00949

§ 371 Date: Oct. 21, 1997

§ 102(e) Date: Oct. 21, 1997

[87] PCT Pub. No.: WO96/33212

PCT Pub. Date: Oct. 24, 1996

[30] Foreign Application Priority Data

Apr. 21, 1995 [JP] Japan .................................. 7-119090
Apr. 21, 1995 [JP] Japan .................................. 7-119091

[51] Int. Cl.⁶ .............................. C07K 5/00; C07K 7/00; A61K 38/00
[52] U.S. Cl. ............................. 514/18; 530/330; 514/17
[58] Field of Search .......................... 514/18, 17, 307, 514/422, 365; 530/330, 331; 546/146; 548/518, 540, 200, 201, 204

[56] References Cited

U.S. PATENT DOCUMENTS

| | | | |
|---|---|---|---|
| 4,816,444 | 3/1989 | Pettit et al. | 514/17 |
| 4,978,744 | 12/1990 | Pettit et al. | 530/330 |
| 5,635,483 | 6/1997 | Pettit et al. | 514/17 |
| 5,654,399 | 8/1997 | Sakakibara et al. | 530/330 |
| 5,741,892 | 4/1998 | Barlozzari et al. | 530/330 |

FOREIGN PATENT DOCUMENTS

| | | |
|---|---|---|
| 0600744 | 6/1994 | European Pat. Off. . |
| 7-70173 | 3/1995 | Japan . |
| WO93/03054 | 2/1993 | WIPO . |
| WO95/09864 | 4/1995 | WIPO . |

OTHER PUBLICATIONS

Pettit et al., "The Isolation and Structure of a Remarkable Marine Animal Antineoplastic Constituent: Dolastatin 10", J. Am. Chem. Soc. 1987, 109, 6883–6885.

*Primary Examiner*—Joseph K. McKane
*Attorney, Agent, or Firm*—Wenderoth, Lind & Ponack, L.L.P.

[57] ABSTRACT

This invention relates to peptide derivatives of the formula

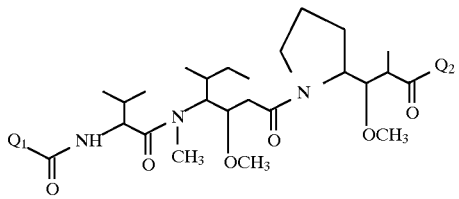

or salts thereof, wherein:

(a) $Q_1$ represents a 1-dimethylamino-2-methylpropyl group and $Q_2$ represents an (R)- or (S)-2-hydroxy-2-phenylethylamino group, a 2-phenylcyclopropylamino group or a 1,2,3,4-tetrahydroisoquinolin-2-yl group, or (b) $Q_1$ represents a 1-methyl-2-pyrrolidinyl group and $Q_2$ represents

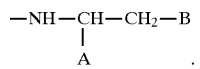

7 Claims, No Drawings

PEPTIDE DERIVATIVES

This application is a 371 of PCT/JP96/00949 filed Apr. 8, 1996.

TECHNICAL FIELD

This invention relates to novel peptide derivatives having an antitumor activity and, more particularly, to peptide derivatives of the formula

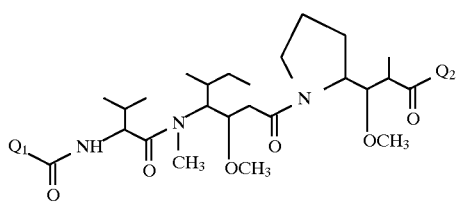
(I)

or salts thereof, wherein:

(a) $Q_1$ represents a 1-dimethylamino-2-methylpropyl group and $Q_2$ represents an (R)- or (S)-2-hydroxy-2-phenylethylamino group, a 2-phenylcyclopropylamino group or a 1,2,3,4-tetrahydroisoquinolin-2-yl group, or heterocyclic group which may further contain one heteroatom selected from S, O and N, and B represents a phenyl group which may optionally be substituted by a halogen atom, hydroxyl group, lower alkyl group or lower alkoxy group.

BACKGROUND ART

Up to now, several compounds having a cell growth inhibiting activity and/or an antineoplastic activity have been isolated from a marine mollusk (*Dolabella auricularia*) which is akin to the sea hare, and these compounds are called dolastatins 1–15. Among them, dolastatin 10 is a pentapeptide extracted from the Indian Ocean (sea hare *Dolabella auricularia*) by Pettit in 1987 and having the structural formula given below, and is known to be a compound having the most powerful cell growth inhibiting activity of all the existing compounds (see Pettit et al., Journal of the American Chemical Society, Vol. 109, p. 6883, 1987 and U.S. Pat. No. 4,816,444).

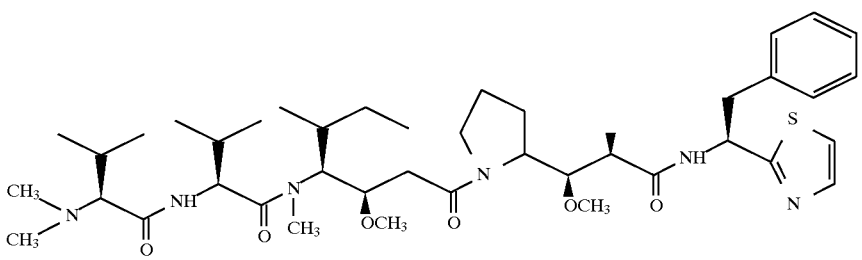

[Dolastatin 10]

(b) $Q_1$ represents a 1-methyl-2-pyrrolidinyl group and $Q_2$ represents

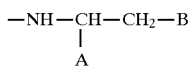

where

A represents a hydrogen atom or

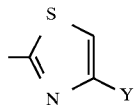

in which Y represents a hydrogen atom or —$COR_1$, and $R_1$ represents a hydroxyl group, a lower alkoxy group, an aralkyloxy group or

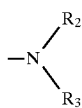

in which $R_2$ and $R_3$ may be the same or different and each represents a hydrogen atom, a lower alkyl group, a phenyl group, or a four- to seven-membered heterocyclic group containing one or two heteroatoms selected from S, O and N, or $R_2$ and $R_3$, together with the nitrogen atom to which they are attached, may form a four- to seven-membered Thereafter, the total synthesis of dolastatin 10 was also reported (see U.S. Pat. No. 4,978,744).

Meanwhile, the present inventors previously disclosed certain derivatives of dolastatin 10 (see the pamphlets of WO 93/03054 and WO 95/09864).

Now, the present inventors have found that (a) certain derivatives of dolastatin 10 obtained by replacing the dolaphenine [α-(thiazoly)phenethylamine] located at the C-terminus of dolastatin 10 by another substituent group and (b) certain derivatives of dolastatin 10 obtained by replacing the dolavaline (N,N-dimethylvaline) located at the N-terminus of dolastatin 10 by N-methylproline have a far more powerful antitumor activity than dolastatin 10.

DISCLOSURE OF THE INVENTION

The term "lower" as used herein means that the groups or compounds modified by this term have not more than six carbon atoms and preferably not more than four carbon atoms.

In the above formula (I), examples of the "lower alkyl group" include methyl, ethyl, n-propyl, isopropyl, n-butyl, isobutyl, sec-butyl, tert-butyl and n-hexyl groups, and examples of the "lower alkoxy group" include methoxy, ethoxy, n-propoxy, isopropoxy and n-butoxy groups. Moreover, the "aralkyloxy group" means an aryl-(lower alkyl)oxy group, and examples thereof include benzyloxy and phenetyloxy. The "halogen atoms" include fluorine, chlorine, bromine and iodine atoms.

When $R_2$ or $R_3$ represents "a four- to seven-membered heterocyclic group containing one or two heteroatoms selected from S, O and N," examples of the heterocyclic group include azetidinyl, furyl, thienyl, pyridyl, piperidinyl, azepinyl, thiazolyl, imidazolyl, oxazolyl, pyrimidinyl and pyridazinyl groups. On the other hand, when $R_2$ and $R_3$, together with the nitrogen atom to which they are attached, form a four- to seven-membered heterocyclic group which may further contain one heteroatom selected from S, O and N," examples of the heterocyclic group include azetidino, pyrrolidino, piperidino, 1-perhydroazepinyl, piperazino, morpholino, and thiomorpholino groups.

Thus, examples of the group

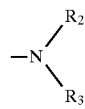

include amino, methylamino, ethylamino, isopropylamino, tert-butylamino, dimethylamino, diethylamino, phenylamino, N-methyl-N-phenylamino, furylamino, pyridylamino, 2-thiazolylamino, imidazolylamino, pyrimidylamino, pyrrolidino, piperidino and morpholino groups.

The "phenyl group which may optionally be substituted by a halogen atom, hydroxy group, lower alkyl group or lower alkoxy group"as represented by the symbol B means an unsubstituted phenyl group or a phenyl group substituted by one halogen atom, hydroxy group, lower alkyl group or lower alkoxy group, and examples thereof include phenyl, 2-fluorophenyl, 2-chlorophenyl, 2-bromophenyl, 3-fluorophenyl, 3-iodophenyl, 4-fluorophenyl, 4-chlorophenyl, 4-bromophenyl, 2-hydroxyphenyl, 4-hydroxyphenyl, 2-methylphenyl, 4-ethylphenyl, 2-methoxyphenyl and 4-ethoxyphenyl.

A group of preferred compounds in accordance with the present invention are the compounds of the above formula (I) wherein $Q_1$ represents a 1-dimethylamino-2-methylpropyl group and $Q_2$ represents an (R)- or (S)-2-hydroxy-2-phenylethylamino group.

Another group of preferred compounds in accordance with the present invention are the compounds of the above formula (I) wherein $Q_2$ represents

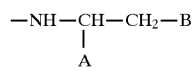

where A is a hydrogen atom and B is a phenyl group which may optionally be substituted by a halogen atom (in particular, a fluorine atom).

Still another group of preferred compounds in accordance with the present invention are the compounds of the above formula (I) wherein $Q_2$ represents

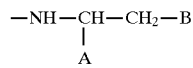

in which A is a 2-thiazolyl group which may optionally be substituted by an N-(lower alykyl)carbamoyl group, and B is an unsubstituted phenyl group.

In the compounds of the above formula (I) in accordance with the present invention, the carbon atoms to which an isopropyl, sec-butyl, methoxy or methyl group is attached are asymmetric carbon atoms and can hence have any (R)- or (S)-steric configuration. Although all such compounds are within the scope of the present invention, compounds having the same steric configuration as dolastatin 10 are preferred from the viewpoint of pharmacological activity.

The peptide compounds of the above formula (I) can also exist in the form of salts. Examples of such salts include hydrochlorides, hydrobromides, trifluoroacetates, p-toluenesulfonates and acetates.

In the practice of the present invention, the peptide compounds of the above formula (I) may be prepared by condensing appropriate amino acids or peptide fragments, for example, according to a liquid phase synthetic method (see E. Schröder and K. Lübke, "The Peptides". Vol. 1, pp. 76–136, 1965, Academic Press) which is well known in the field of peptide chemistry.

For example, in order to avoid racemization during condensation, it is suitable to synthesize the peptide compounds by condensing a tripeptide fragment of the following formula (II)

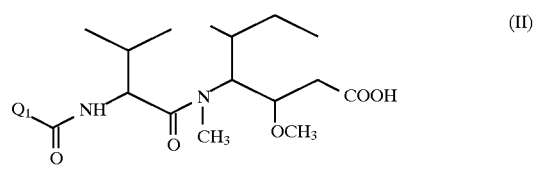

wherein $Q_1$ has the same meaning as described previously, with a fragment of the following formula (III)

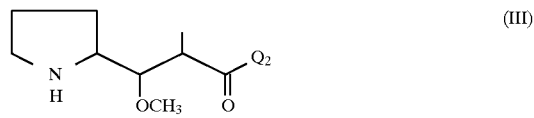

wherein $Q_2$ has the same meaning as described previously.

Moreover, in order to synthesize many of the compounds of the present invention efficiently, it is preferable to condense a tetrapeptide fragment of the following formula (IV)

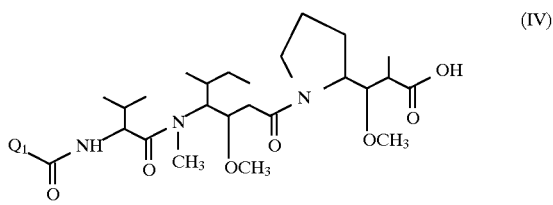

wherein $Q_1$ has the same meaning as described previously, with a fragment of the following formula (V)

wherein $Q_2$ as the same meaning as described previously.

The condensation reactions may generally be carried out by treatment with a condensing agent such as dicyclohexylcarbodiimide (DOC), diphenylphosphoryl azide (DPPA), diethyl cyanophosphate (DEPC) or BOP reagent, in an inert solvet such as chloroform, ethyl acetate, tetrahydrofuran (THF), dimethylformamide (DMF) or acetonitrile, and in the presence of an organic base such as triethylamine, N-methylmorpholine or diisopropylethylamine (DIEA), if necessary.

The reaction temperature usually ranges from $-10°$ C. to room temperature and is preferably around $0°$ C. As to the proportions in which the compound of formula (III), the organic base and the condensing agent are used relative to the compound of formula (II), it is advantageous to use at least 1 mole, preferably about 1.0–1.1 moles, of the compound of formula (III), about 1–2 moles of the organic base, and about 1 mole of the condensing agent, per mole of the compound of formula (II).

The reaction of the compound of formula (IV) with the compound of formula (V) may be carried out under the same conditions as described above for the reaction of the compound of formula (II) with the compound of formula (III).

The compounds of formula (I) wherein Y is a carboxyl group may also be prepared by hydrolyzing a compound of formula (I) wherein Y is a (lower alkoxy)carbonyl group, in the presence of an alkali.

The peptide compounds of formula (I) formed in the above-described manner may be isolated from the reaction mixture and purified by recrystallization, ion-exchange chromatography, gel filtration, high-performance liquid chromatography or the like.

Most of the compounds of the above formulas (II), (III) and (IV) used as starting materials in the above-described reactions are novel compounds which have not hitherto been described in the literature. However, they may readily be prepared by condensing their constituent amino acids according to the liquid phase synthetic method.

The compounds of formula (I) in accordance with the present invention have a more powerful antitumor activity than that of dolastatin 10, and also have high therapeutic ratios. Accordingly, they are useful for the treatment or therapy of, for example, leukemia, non-small cell carcinoma of the lungs, small cell carcinoma of the lungs, cancer of the colon, cancer of the CNS, melanoma, ovarian carcinoma, cancer of the kidneys, cancer of the stomach, and cancer of the urinary bladder.

The antitumor activity of the compounds of formula (I) in accordance with the present invention can be determined in the following manner.

0.1 ml ($10^6$ cells per mouse) each of mouse leukemia P388 cells was transplanted into the abdominal cavity of 7-weeks-old CDF1 mice. On the first day (the next day) and the fifth day after transplantation, a drug was administered intraperitoneally and the life or death of the mice was observed for 60 days. Then, the percent increase in life-span (ILS) was calculated from the results of observation according to the following equation. In the following equation, T designates the median number of days for which the mice of the drug-treated group survived, and C designates the median number of days for which the mice of the control group survived.

$$ILS = \frac{T-C}{C} \times 100$$

The results thus obtained are shown in the following table. The antitumor activity of each drug is expressed as a relative value based on the antitumor activity of dolastatin 10 for which ILS is regarded as 1.

TABLE

| Example No. of compound | Antitumor activity |
| --- | --- |
| Example 1 | 1.5 |
| Example 2 | 1.9 |
| Example 9 | 1.3 |
| Dolastatin 10 | 1 |

When the compounds of the present invention are used as drugs, they may be formulated in any of various pharmaceutical preparations according to the intended purpose. These pharmaceutical preparations include solid preparations such as tablets, hard capsules, soft capsules, granules, powders, subtilized granules, pills and troches; semisolid preparations such as suppositories and ointments; and liquid preparations such as injections, emulsions, suspensions, lotions and sprays. Non-toxic additives which can be used in the aforesaid pharmaceutical preparations include, for example, starch, gelatin, glucose, lactose, fructose, maltose, magnesium carbonate, talc, magnesium stearate, methylcellulose, carboxymethylcellulose and salts thereof, acacia, polyethylene glycol, alkyl esters of p-hydroxybenzoic acid, syrup, ethanol, propylene glycol, petrolatum, carbowax, glycerin, sodium chloride, sodium sulfite, sodium phosphate and citric acid. The aforesaid pharmaceutical preparations may also contain other therapeutically effective drugs.

The content of the compounds of the present invention in the aforesaid pharmaceutical preparations may vary according to the dosage form. Generally, it is desirable that solid and semisolid preparations contain the compounds of the present invention in an amount of 0.1 to 50% by weight and liquid preparations contain them in an amount of 0.05 to 10% by weight.

The dosage of the compounds of the present invention may vary widely according to the type of the warm-blooded animal (including human beings) to be treated, the route of administration, the severity of symptoms, the diagnostic judge by the doctor, and the like. Generally, they may be administered in a daily dose of about 0.01 to 50 mg/kg. However, it is a matter of course that they may be administered in doses less than the lower limit of the aforesaid range or greater than the upper limit thereof, depending on the severity of symptoms in the patient and the diagnostic judge by the doctor. The aforesaid daily dose may be given at a time or in several divided doses.

EXAMPLES

The present invention is more specifically explained with reference to the following reference examples and examples.

As to the structures of the compounds corresponding to the compound numbers used in the reference examples and examples, see the following flow sheets 1 to 3. In these flow sheets, Bu$^t$, Boc, Bzl, Z and Me represent tert-butyl, tert-butoxycarbonyl, benzyl, benzyloxycarbonyl and methyl groups, respectively. $Q_2$, B and Y have the same meanings as described previously.

Flow sheet 1
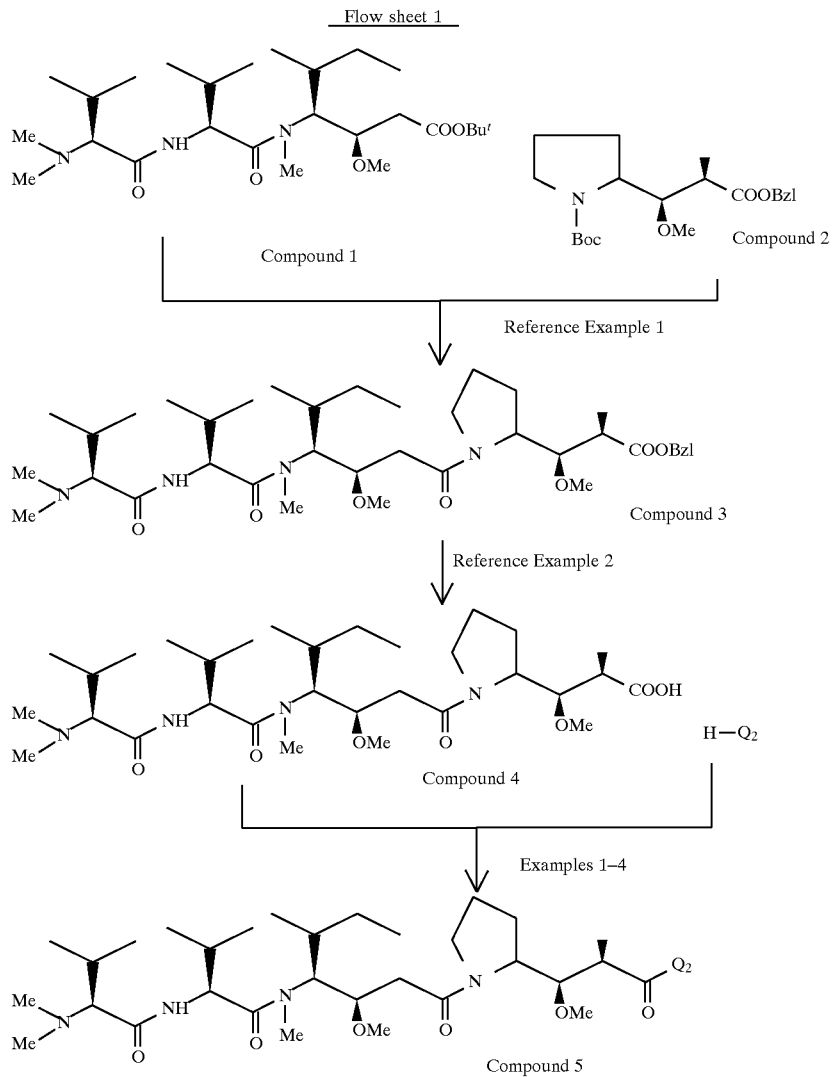
Flow sheet 2
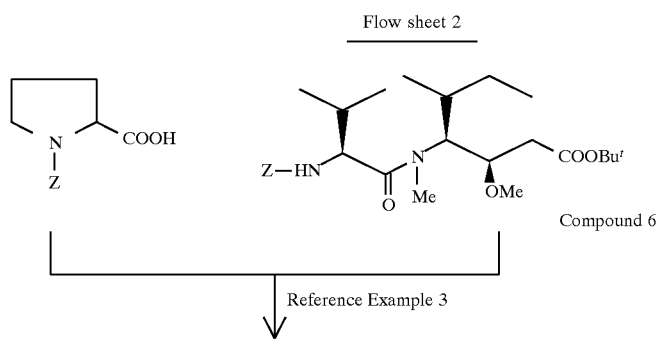

-continued
Flow sheet 2
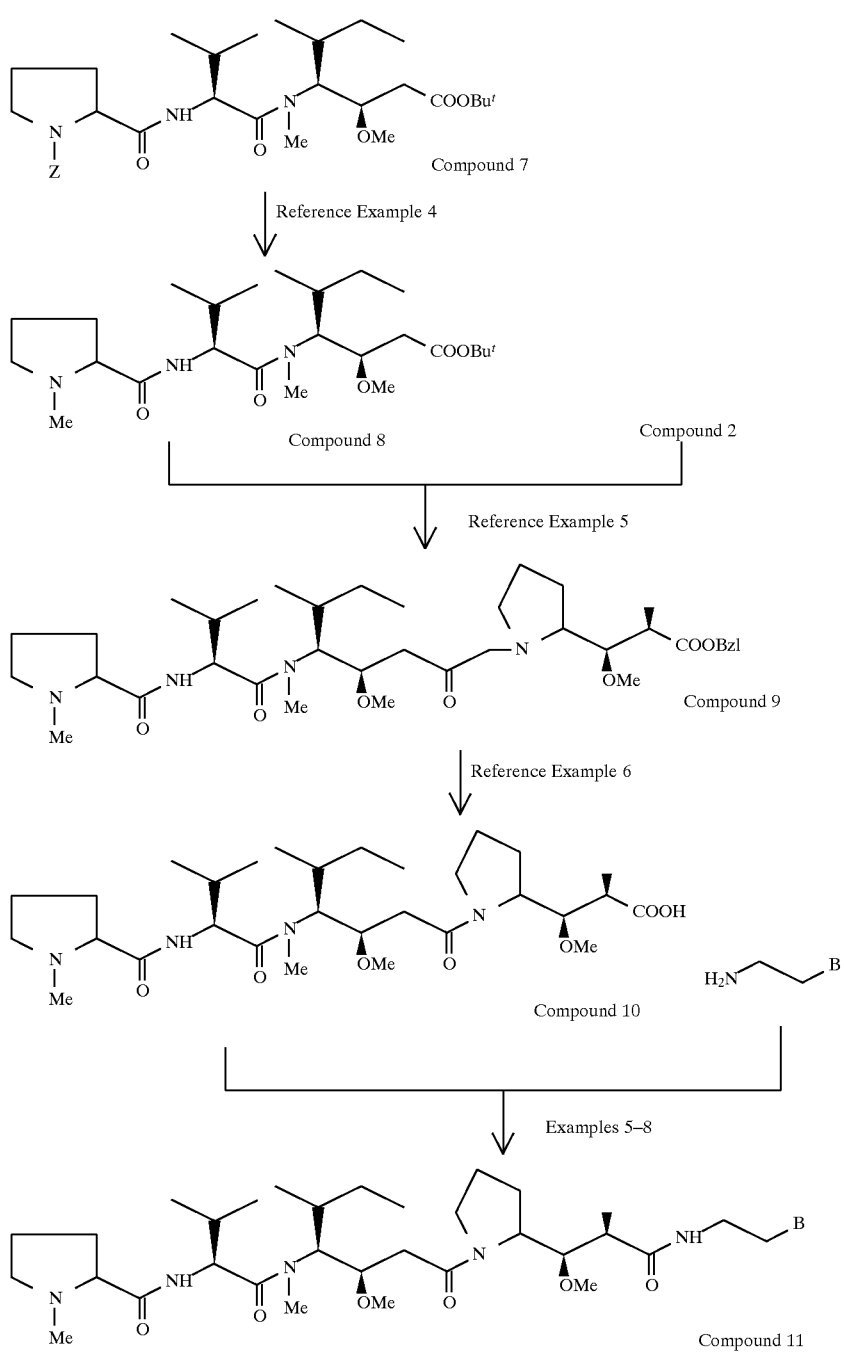

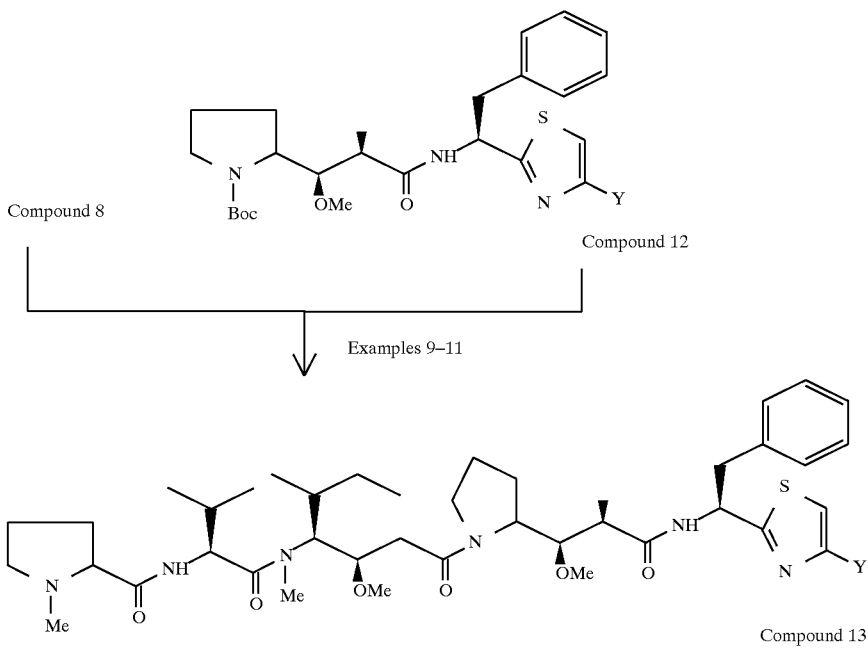

Flow sheet 3

Compound 8

Compound 12

Examples 9–11

Compound 13

Reference Example 1

830.7 mg (1.71 millimoles) of compound 1 was dissolved in 20 ml of 50% trifluoroacetic acid/dichloromethane under cooling with ice. This solution was stirred at room temperature for 2 hours and then evaporated to dryness under reduced pressure. After the residue was dissolved in 5 ml of dimethylformamide (DMF), 2.4 ml of triethylamine was added thereto under cooling with ice and the resulting mixture was evaporated to dryness under reduced pressure.

On the other hand, 644.3 mg (1.71 millimoles) of compound 2 was dissolved in 8.6 ml of 4N hydrogen chloride/dioxane under cooling with ice. This solution was stirred at room temperature for 1.5 hours and then evaporated to dryness under reduced pressure.

Both of the above residues were combined and dissolved in 7 ml of DMF. While this solution was being stirred under cooling with ice, 352 mg (2.16 millimoles) of diethyl cyanophosphate (DEPC) and 0.53 ml (3.82 millimoles) of triethylamine were added thereto and the resulting mixture was stirred overnight at temperatures ranging from 0° to room temperature. The reaction mixture was diluted with an ethyl acetate-benzene (4:1) mixture, washed with a saturated aqueous solution of sodium bicarbonate and a saturated aqueous solution of sodium chloride, and then dried. After the solvent was distilled off, the remaining oily matter (1.35 g) was purified by Sephadex LH-20 column chromatography using hexane-methanol-dichloromethane (4:5:15) as the eluent. Thus, 1.06 g of the desired compound 3 was obtained as an amorphous material (in a 89.7% yield).

$[\alpha]^{28}_D$–48.2 ° (c=0.375, MeOH)

$^1$H-NMR (CDCl$_3$, δ): 0.7–1.1(m), 1.27(3H, d, J=6.8 Hz), 1.6–2.2(m), 2.25(6H, s), 2.3–2.6(m), 3.02(3H, s), 3.30(3H, s), 3.35(3H, s), 3.9–4.3(m), 4.80(1H, dd, J=9.2 Hz, 6.4 Hz), 5.13(2H, s), 6.86(1H, br. d), 7.34(5H, s).

Reference Example 2

688 mg (1.00 millimole) of compound 3 was dissolved in 10 ml of t-butanol-water (9:1), and 0.1 g of 5% palladium-carbon was added thereto. This mixture was stirred in a stream of hydrogen for 5 hours. After the catalyst was filtered off and washed, the filtrate and the washings were combined and evaporated to dryness under reduced pressure. Thus, 590 mg of the desired compound 4 was obtained as colorless foamy material (in a 98.7% yield).

$[\alpha]^{28}_D$–57.3° (c=0.955, MeOH)

$^1$H-NMR (CDCl$_3$, δ): 0.7–1.1(m), 1.17 (3H, d, J=4.4 Hz), 1.6–2.2(m), 2.54(6H, s), 3.04 and 3.08(3H, s), 3.27 and 3.31(3H, s), 3.36 and 3.42(3H, s), 4.0–4.3(m), 4.6–5.0(m), 5.0–5.4(m), 6.97(1H, br. d).

Example 1

30 mg (50 micromoles) of compound 4 and 10 mg (58 micromoles) of (R)-2-hydroxy-2-phenylethylamine hydrochloride were dissolved in 0.5 ml of DMF. While this solution was being stirred under cooling with ice, 9.5 mg (58 micromoles) of DEPC and 16 μl (11.5 micromoles) of triethylamine were added thereto and the resulting mixture was stirred overnight at temperatures ranging from 0° to room temperature. The reaction mixture was diluted with dichloromethane, washed with a saturated aqueous solution of sodium bicarbonate and a saturated brine, and then dried. After the solvent was distilled off, the resulting residue was purified by preparative TLC [developing solvent: dichloromethane-methanol (10:1)] and then by Sephadex LH-20 column chromatography using hexane-methanol-dichloromethane (4:5:15) as the eluent. Thus, 25.1 mg of the desired compound 5-A (i.e., compound 5 in which Q is an (R)-2-hydroxy-2-phenylethylamino group) was obtained as an amorphous material (in a 69.9% yield).

$[\alpha]^{28}_D$–43.8° (c=0.319, MeOH)

$^1$H-NMR (CDCl$_3$, δ): 0.7–1.1(m), 1.27(3H, d, J=7.0 Hz), 1.6–2.2(m), 2.27(6H, s), 2.3–2.6(m), 3.02(3H, s), 3.32(3H, s), 3.43(3H, s), 3.82(1H, br. d), 4.0–4.2(m), 4.77(1H, dd, J=9.0 Hz, 6.8 Hz), 6.6–7.0(m), 7.2–7.5(5H, m).

Example 2

Using compound 4 and (S)-2-hydroxy-2-phenylethylamine, compound 5-B (i.e., compound 5 in which $Q_2$ is an (S)-2-hydroxy-2-phenylethylamino group) was obtained (in a 79.1% yield) in the same manner as described in Example 1.

$[\alpha]^{28}_D$ −44.5° (c=0.330, MeOH)

$^1$H-NMR (CDCl$_3$, δ): 0.7–1.1(m), 1.26(3H, d, J=7.0 Hz), 1.5–2.2(m), 2.65 (6H, s), 3.02 (3H, s), 3.32 (3H, s), 3.40(3H, s), 3.85(1H, dd, J=9.5 Hz, 1.5 Hz), 4.0–4.2(m), 4.71(1H, dd, J=8.1 Hz, 6.8 Hz), 4.8–5.1(m), 6.7–6.9(m), 7.2–7.5(5H, m).

Example 3

Using compound 4 and dl-trans-2-phenylcyclopropylamine, compound 5-C (i.e., compound 5 in which $Q_2$ is a 2-phenylcyclopropylamino group) was obtained (in a 82.1% yield) in the same manner as described in Example 1.

$[\alpha]^{24}_D$ −52.4° (c=0.354, MeOH)

$^1$H-NMR (CDCl$_3$, δ): 0.7–1.2(m), 1.2–1.4(m), 1.6–2.2 (m), 2.37 (6H, s), 3.02 (3H, s), 3.33 and 3.35 (3H, s), 3.41(3H, s), 3.8–4.3(m), 4.76(1H, dd, J=8.7 Hz, 6.9 Hz), 7.26(5H, s).

Example 4

Using compound 4 and 1,2,3,4-tetrahydroisoquinoline, compound 5-D (i.e., compound 5 in which $Q_2$ is a 1,2,3,4-tetrahydroisoquinolin-2-yl group) was obtained (in a 66.2% yield) in the same manner as described in Example 1.

$[\alpha]^{23}_D$ −48.2° (c=0.320, MeOH)

$^1$H-NMR (CDCl$_3$, δ): 0.6–1.1(m), 1.1–1.3(m), 1.5–2.2 (m), 2.55(6H, s), 2.7–3.0(m), 3.00(3H, s), 3.30(3H, s), 3.44(3H, s), 3.55–4.0(m), 4.0–4.3(m), 4.5–5.0(m), 7.15 and 7.19(4H, s).

Reference Example 3

0.85 g (1.73 millimoles) of compound 6 was dissolved in 15 ml of t-butanol-water (9:1), and 0.1 g of 5% palladium-carbon was added thereto. This mixture was stirred in a stream of hydrogen. After 3 hours' reaction, the catalyst was filtered off and washed, and the filtrate and the washings were combined and evaporated to dryness under reduced pressure. The residue was dissolved in 20 ml of benzene, and this solution was evaporated to dryness under reduced pressure. This procedure was repeated once more to obtain oily matter. This oily matter, together with 0.48 g (1.93 millimoles) of Z-proline and 0.31 g (1.90 millimoles) of diethyl cyanophosphate (DEPC), was dissolved in 10 ml of dimethylformamide (DMF). While this solution was being stirred under cooling with ice, a solution of 0.19 g (1.88 millimoles) of triethylamine in 1 ml of DMF was added dropwise thereto.

Thereafter, the stirring was continued at 0° C. for 4 hours and at room temperature overnight. The resulting clear reaction mixture was fully diluted with ethyl acetate, washed with ice-cold 2N hydrochloric acid and a saturated aqueous solution of sodium bicarbonate, and then dried. The solvent was distilled off under reduced pressure to obtain 1.01 g of oily material. This oily material was purified by silica gel column chromatography [eluent: ethyl acetate-hexane (2:1) ]. Thus, 0.97 g of the desired compound 7 was obtained as a colorless foamy material (in a 95.1% yield).

$[\alpha]^{27}_D$ −81.7° (c=1.025, MeOH)

$^1$H-NMR (CDCl$_3$, δ): 0.75–1.05(12H, m), 1.46(9H, s), 1.8–2.2(4H, m), 2.3–2.4(2H, m), 2.96(3H, s), 3.34(3H, s), 3.4–3.6(2H, m), 3.8–4.0(1H, m), 4.2–4.4(1H, m), 4.73(1H, dd, J=8.9 Hz, 6.3 Hz), 5.17(2H, br. s), 7.32(5H, s).

Reference Example 4

0.50 g (0.85 millimole) of compound 7 was dissolved in 20 ml of methanol, and 1.0 g of 37% formalin and 0.4 g of 5% palladium-carbon were added thereto. This mixture was stirred in a stream of hydrogen for 48 hours. After the catalyst was filtered off and washed with methanol, the filtrate and the washings were combined and evaporated to dryness under reduced pressure. The resulting oily material was dissolved in ethyl acetate-hexane (1:1), and any insoluble material was removed by filtration. After the filtrate was evaporated to dryness under reduced pressure, the remaining oily material was purified by silica gel column chromatography [eluent: ethyl acetate-hexane (2:1)]. Thus, 0.36 g of the desired compound 8 was obtained as a colorless oily material (in a 90.0% yield).

$[\alpha]^{25}_D$ −76.2° (c=1.10, MeOH)

$^1$H-NMR (CDCl$_3$, δ): 0.7–1.05(12H, m), 1.46(9H, s), 1.6–1.9(4H, m), 2.31(3H, s), 2.3–2.45(2H, m), 2.99(3H, s), 3.36(3H, s), 3.75–4.0(1H, m), 4.73(1H, dd, J=8.9 Hz, 7.1 Hz), 7.81(1H, br. d).

Reference Example 5

310 mg (0.66 millimole) of compound 8 was dissolved in 50% trifluoroacetic acid/dichloromethane at 0° C. This solution was stirred at room temperature for 1 hour and then evaporated to dryness under reduced pressure.

On the other hand, 263 mg (0.70 millimole) of compound 2 was dissolved in 4N hydrogen chloride/dioxane at 0° C. This solution was stirred at room temperature for 1 hour and then evaporated to dryness under reduced pressure. After the residue was dissolved in 3 ml of DMF, 0.9 ml of triethylamine was added thereto under cooling with ice and the resulting mixture was evaporated to dryness under reduced pressure. After these residues were combined and dissolved in 3 ml of DMF, 136 mg (0.83 millimole) of DEPC and 0.11 ml (0.79 millimole) of triethylamine were added thereto under cooling with ice and the resulting mixture was allowed to stand overnight with stirring.

The reaction mixture was diluted with an ethyl acetate-benzene (4:1) mixture, washed with a saturated aqueous solution of sodium bicarbonate and a saturated brine, and then dried. After the solvent was distilled off to obtain 449 mg of oily material. This oily material was purified by silica gel column chromatography [eluent: dichloromethane-methanol (30:1→10:1)]. Thus, 185 mg of the desired compound 9 was obtained as a colorless oily material (in a 41.5% yield).

$[\alpha]_D$ n.d.

$^1$H-NMR (CDCl$_3$, δ): 0.7–1.1(m), 1.27(3H, d, J=7.0 Hz), 1.5–2.3(m), 2.34 (3H, s), 2.3–2.9 (m), 3.00 (3H, s), 3.30(3H, s), 3.35(3H, s), 3.85–4.3(m), 4.68(1H, dd, J=8.7 Hz, 4.9 Hz), 5.13(2H, s), 7.34(5H, s).

Reference Example 6

185 mg of compound 9 was dissolved in 3 ml of t-butanol-water (9:1), and 40 mg of 5% palladium-carbon was added thereto. This mixture was stirred in a stream of hydrogen for 5 hours. After the catalyst was filtered off and washed, the filtrate and the washings were combined and evaporated to dryness under reduced pressure. Thus, 155 mg of the desired compound 10 was obtained as a colorless oily material (in a 97.1% yield).

$[\alpha]_D$ −83.3° (c=0.365, MeOH)

Example 5

23.4 mg (40 micromoles) of compound 10 and 12.1 mg (100 micromoles) of phenethylamine were dissolved in 0.5 ml of DMF. While this solution was being stirred under cooling with ice, 9.6 mg (59 micromoles) of DEPC and 8 μl of triethylamine were added thereto and the resulting mixture was allowed to stand overnight with stirring. The reaction mixture was diluted with dichloromethane, washed with a saturated aqueous solution of sodium bicarbonate and a saturated aqueous solution of sodium chloride, and then dried. The solvent was distilled off to obtain 23.0 mg of residue. This residue was purified by Sephadex LH-20 column chromatography [eluent: hexane-methanol-dichloromethane (4:5:15)]. Thus, 18.8 mg of the desired compound 11-A (i.e., compound 11 in which B is a phenyl group) was obtained as a colorless waxy material (in a 68.6% yield).

$[\alpha]^{25}_D$ -61.0° (c=0.39, MeOH)

$^1$H-NMR (CDCl$_3$, δ): 0.7–1.1(m), 1.21(3H, d, J=7.0 Hz), 1.5–2.2(m), 2.38(3H, s), 2.83(2H, t, J=7.0 Hz), 3.01 (3H, s), 3.32(3H, s), 3.36(3H, s), 3.2–3.6(m), 3.84(1H, dd, J=7.9 Hz, 2.2 Hz), 3.9–4.2(m), 4.71(1H, dd, J=9.2 Hz, 7.0 Hz), 6.3–6.6 (m), 7.23(5H, s), 7.7–8.1(1H, m).

The compounds of Examples 6–8 were obtained by reacting compound 10 with phenethylamine derivatives in the same manner as described in Example 5.

Example 6

Compound 11-B (i.e., compound 11 in which B is a 2-fluorophenyl group) was obtained as a waxy material (in a 73.0% yield).

$[\alpha]^{28}_D$ -61.7° (c=0.326, MeOH)

$^1$H-NMR (CDCl$_3$, δ): 0.7–1.1(m), 1.21(3H, d, J=7.1 Hz), 1.5–2.3(m), 2.33(3H, s), 2.3–2.6(m), 2.88(2H, t, J=7.3 Hz), 3.01(3H, s), 3.32(3H, s), 3.37(3H, s), 3.2–3.7(m), 3.84(1H, dd, J=8.0 Hz, 2.5 Hz), 3.9–4.2(br), 4.5–4.9(1H, m), 6.4–6.6 (1H, m), 6.8–7.3(4H, m), 7.6–8.1(1H, m).

Example 7

Compound 11-C (i.e., compound 11 in which B is a 3-fluorophenyl group) was obtained as an amporphous powder (in a 70.9% yield).

$[\alpha]^{28}_D$ -56.7° (c=0.287, MeOH)

$^1$H-NMR (CDCl$_3$, δ): 0.7–1.1(m), 1.22(3H, d, J=7.0 Hz), 1.5–2.2(m), 2.34(3H, s), 2.3–2.7(m), 2.84(2H, t, J=6.8 Hz), 3.02(3H, s), 3.32(3H, s), 3.36(3H, s), 3.3–3.6(m), 3.83(1H, dd, J=8.4 Hz, 2.2 Hz), 3.9–4.3(m), 4.5–4.9(m), 6.5–6.7(1H, m), 6.8–7.2(4H, m), 7.7–8.1(1H, m).

Example 8

Compound 11-D (i.e., compound 11 in which B is a 4-fluorophenyl group) was obtained as an amorphous powder (in a 72.7% yield).

$[\alpha]^{28}_D$ -55.9° (c=0.285, MeOH)

$^1$H-NMR (CDCl$_3$, δ): 0.7–1.1(m), 1.22(3H, d, J=7.3 Hz), 1.5–2.2(m), 2.34(3H, br. s), 2.80(2H, t, J=7.0 Hz), 3.01(3H, s), 3.32(3H, s), 3.36(3H, s), 3.2–3.6(m), 3.75–3.95(1H, m), 3.95–4.3(m), 4.5–4.9(m), 6.4–6.6(1H, m), 6.8–7.2(4H, m).

Example 9

0.4 ml of 50% trifluoroacetic acid/dichloromethane was added to 14.8 mg (32 micromoles) of compound 8 under cooling with ice. This mixture was stirred at room temperature for 4 hours and then evaporated to dryness by flushing with nitrogen gas. On the other hand, 14.3 mg (30 micromoles) of compound 12-A (i.e., compound 12 in which Y is a hydrogen atom) was treated with 0.4 ml of 50% trifluoroacetic acid/dichloromethane in the same manner as described above. Then, this mixture was evaporated to dryness. After both of these residues were combined and dissolved in 1 ml of DMF, 85 μl of triethylamine was added thereto under cooling with ice and the resulting mixture was evaporated to dryness under reduced pressure. The resulting residue was dissolved again in 0.4 ml of DMF. While this solution was being stirred under cooling with ice, 6.7 mg (41 micromoles) of DEPC and 10 μl (72 micromoles) of triethylamine were added thereto and the resulting mixture was allowed to stand overnight with stirring.

The reaction mixture was evaporated to dryness under reduced pressure. After the residue was dissolved in dichloromethane, this solution was washed with a saturated aqueous solution of sodium bicarbonate and a saturated brine, and then dried. After the solvent was distilled off, the resulting residue was purified by preparative TLC [developing solvent: dichloromethanemethanol (10:1)]. Thus, 14.5 mg of the desired compound 13-A (i.e., compound 13 in which Y is a hydrogen atom) was obtained as a white powder (in a 62.0% yield).

$[\alpha]^{25}_D$ -92.4° (c=0.218, MeOH)

$^1$H-NMR (CDCl$_3$, δ): 0.7–1.2(m), 1.22(3H, d, J=7.0 Hz), 1.5–2.0(m), 2.35 (3H, s), 3.01 (3H, s), 3.33 (3H, s), 3.36(3H, s), 3.89(1H, dd, J=7.0 Hz, 2.2 Hz), 4.0–4.3(1H, m), 4.66(1H, dd, J=7.9 Hz, 6.6 Hz), 5.5–5.7(1H, m), 7.21(5H, s), 7.73(1H, d, J=3.3 Hz).

Example 10

Compound 8 was reacted with compound 12-B (i.e., compound 12 in which Y is a methoxycarbonyl group) in the same manner as described in Example 9. Thus, compound 13-B (i.e., compound 13 in which Y is a methoxycarbonyl group) was obtained as an amorphous solid (in a 78.2% yield).

$[\alpha]_D$ n.d.

$^1$H-NMR (CDCl$_3$, δ): 0.7–1.1(m), 1.11(3H, d, J=7.0 Hz), 1.5–2.1(m), 2.35(3H, s), 3.02(3H, s), 3.32(3H, s), 3.33(3H, s), 3.95(3H, s), 3.8–4.3(m), 4.70(1H, dd, J=7.5 Hz, 6.8 Hz), 5.4–5.8 (1H, m), 7.23 (5H, s), 8.05 (1H, s).

Example 11

A 70% aqueous solution of ethylamine was added to 38.7 mg (47 micromoles) of compound 13-B under cooling with ice. After completion of the dissolution, the resulting mixture was allowed to stand overnight at room temperature and then evaporated to dryness under reduced pressure. The residue was purified by preparative TLC [developing solvent: dichloromethane-methanol (10:1)] and then by Sephadex LH-20 column chromatography using hexane-methanol-dichloromethane (4:5:15) as the eluent. Thus, 34.8 mg of the desired compound 13-C (i.e., compound 13 in which Y is an N-ethylcarbamoyl group) was obtained as an amorphous solid (in a 88.5% yield).

$[\alpha]^{28}_D$ -81.4° (c=0.309, MeOH)

$^1$H-NMR (CDCl$_3$, δ): 0.7–1.1(m), 1.11(3H, d, J=7.3 Hz), 1.26(3H, t, J=7.3 Hz), 1.5–2.2(m), 2.36(3H, s), 3.02(3H, s), 3.33(6H, s), 3.2–3.7(m), 3.8–4.0(1H, br. dd), 4.0–4.3(m), 4.69(1H, dd, J=8.8 Hz, 6.8 Hz), 5.3–5.7(1H, m), 7.24(5H, s), 7.95(1H, s).

We claim:
1. A peptide compound of the formula

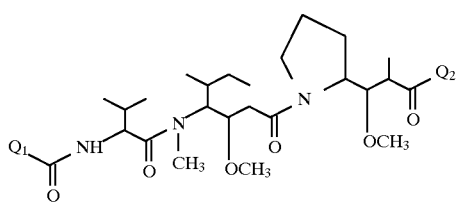

or a salt thereof, wherein:
- (a) $Q_1$ represents a 1-dimethylamino-2-methylpropyl group and $Q_2$ represents an (R)- or (S)-2-hydroxy-2-phenylethylamino group, a 2-phenylcyclopropylamino group or a 1,2,3,4-tetrahydroisoquinolin-2-yl group, or
- (b) $Q_1$ represents a 1-methyl-2-pyrrolidinyl group and $Q_2$ represents

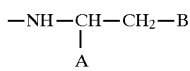

where
A is a hydrogen atom or

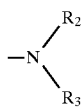

in which Y is a hydrogen atom or —$COR_1$, and $R_1$ is a hydroxyl group, a lower alkoxy group, an aralkyloxy group or

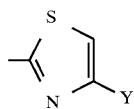

in which $R_2$ and $R_3$ are the same or different and are each a hydrogen atom, a lower alkyl group, a phenyl group, or a four- to seven-membered heterocyclic group having one or two heteroatoms selected from S, O and N, or $R_2$ and $R_3$, together with the nitrogen atom to which they are attached, may form a four- to seven-membered heterocyclic group which may further have one heteroatom selected from S, O and N, and B is a phenyl group which may optionally be substituted by a halogen atom, hydroxyl group, lower alkyl group or lower alkoxy group.

2. A peptide compound or a salt thereof as claimed in claim 1 wherein $Q_1$ represents a 1-dimethylamino-2-methylpropyl group and $Q_2$ represents an (R)- or (S)-2-hydroxy-2-phenylethylamino group.

3. A peptide compound on a salt thereof as claimed in claim 1 wherein $Q_1$ represents a 1-methyl-2-pyrrolidinyl group and $Q_2$ represents

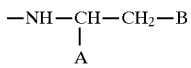

where A is a hydrogen atom and B is a phenyl group which may optionally be substituted by a halogen atom.

4. A peptide compound or a salt thereof as claimed in claim 3 wherein the halogen atom is a fluorine atom.

5. A peptide compound or a salt thereof as claimed in claim 1 wherein $Q_1$ represents a 1-methyl-2-pyrrolidinyl group and $Q_2$ represents

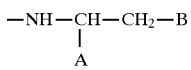

where A is a 2-thiazolyl group which may optionally be substituted by an N-(lower alkyl)carbamoyl group and B is an unsubstituted phenyl group.

6. A pharmaceutical composition comprising an effective amount of a peptide compound or a salt thereof as claimed in claim 1, and a pharmaceutical acceptable additive.

7. A method for treating a tumor in a patient which comprises administering an effective amount of a peptide compound or a salt thereof as claimed in claim 1 to the patient.

* * * * *